United States Patent
Duplantier

[11] Patent Number: 6,028,086
[45] Date of Patent: Feb. 22, 2000

[54] CATECHOL DIETHERS DERIVATIVES USEFUL AS PHARMACEUTICAL AGENTS

[75] Inventor: Allen J. Duplantier, Ledyard, Conn.

[73] Assignee: P Pfizer Inc, New York, N.Y.

[21] Appl. No.: 08/973,725

[22] PCT Filed: Jun. 7, 1995

[86] PCT No.: PCT/US95/07208

§ 371 Date: Jun. 1, 1998

§ 102(e) Date: Jun. 1, 1998

[87] PCT Pub. No.: WO96/40636

PCT Pub. Date: Dec. 19, 1996

[51] Int. Cl.[7] .................. C07D 213/75; A61K 31/44
[52] U.S. Cl. .................. 514/352; 546/297; 546/309
[58] Field of Search .................. 546/297, 309; 514/352

[56] References Cited

FOREIGN PATENT DOCUMENTS

| 497564 | 1/1991 | European Pat. Off. | 546/297 |
| 95/004046 | 2/1995 | WIPO | 546/297 |

*Primary Examiner*—Zinna Northington Davis
*Attorney, Agent, or Firm*—Peter C. Richardson; Paul H. Ginsburg; Jolene W. Appleman

[57] ABSTRACT

A compound of formula (I) wherein a, b, V, W, X, Y, Z, $R^1$ and $R^2$ are as defined above. The compound of formula (I) and the pharmaceutically acceptable salts thereof are useful in inhibiting phosphodiesterase (PDE) type IV and the production of tumor necrosis factor (TNF) and in the treatment of asthma, arthritis, bronchitis, chronic obstructive airways disease, psoriasis, allergic rhinitis, dermatitis and other inflammatory diseases characterized by phosphodiesterase (PDE) type IV activity as well as AIDS, sepsis, septic shock and other diseases, such as cachexia, involving the production of TNF.

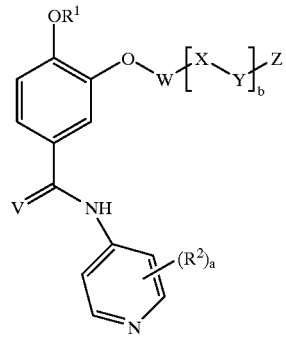

12 Claims, No Drawings

CATECHOL DIETHERS DERIVATIVES USEFUL AS PHARMACEUTICAL AGENTS

This application is a 371 of PCT/US95/07208 filed Jun. 7, 1995.

BACKGROUND OF THE INVENTION

This invention relates to catechol diethers containing a long lipophilic sidechain which are selective inhibitors of phosphodiesterase (PDE) type IV or the production of tumor necrosis factor (TNF) and as such are useful in the treatment of asthma, arthritis, bronchitis, chronic obstructive airways disease, psoriasis, allergic rhinitis, dermatitis and other inflammatory diseases as well as AIDS, sepsis, septic shock and other diseases, such as cachexia, involving the production of TNF. Compounds of the present invention may have combined PDE IV and TNF inhibitory activity.

This invention also relates to a method of using such compounds in the treatment of the above diseases in mammals, especially humans and to pharmaceutical compositions useful therefor.

Since the recognition that cyclic AMP is an intracellular second messenger (E. W. Sutherland, and T. W. Rall, *Pharmacol. Rev.,* 1960, 12, 265), inhibition of the phosphodiesterases has been a target for modulation and, accordingly, therapeutic intervention in a range of disease processes. More recently, distinct classes of PDE have been recognized (J. A. Beavo and D. H. Reifsnyder, *TiPS,* 1990, 11, 150), and their selective inhibition has led to improved drug therapy (C. D. Nicholson, R. A. Challiss and M. Shahid, *TiPS,* 1991, 12, 19). More particularly, it has been recognized that inhibition of PDE type IV can lead to inhibition of inflammatory mediator release (M. W. Verghese et al., *J. Mol. Cell Cardiol.,* 1989, 12 (Suppl. II), S 61) and airway smooth muscle relaxation (T. J. Torphy in *Directions for New Anti-Asthma Drugs,* eds S. R. O'Donnell and C. G. A. Persson, 1988, 37, Birkhauser-Verlag). Thus, compounds that inhibit PDE type IV, but which have poor activity against other PDE types, inhibit the release of inflammatory mediators and relax airway smooth muscle without causing cardiovascular effects or antiplatelet effects.

TNF is recognized to be involved in many infectious and auto-immune diseases, including cachexia (W. Friers, *FEBS Letters,* 1991, 285, 199). Furthermore, it has been shown that TNF is the prime mediator of the inflammatory response seen in sepsis and septic shock (C. E. Spooner et al., *Clinical Immunology and Immunopathology,* 1992, 62, S11).

SUMMARY OF THE INVENTION

The present invention relates to a compound of the formula

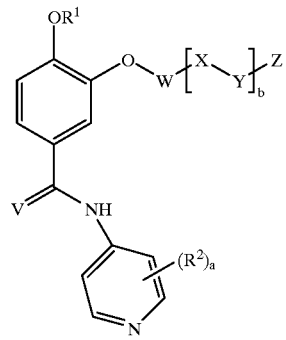

and the pharmaceutically acceptable salts thereof; wherein
a is 0, 1, 2, 3 or 4;
b is 0, 1, 2, 3 or 4;
V is O or S;
W is $(C_2-C_{12})$alkyl or $(C_3-C_{12})$alkenyl;
X is O or $NR^3$;
Y is $(C_1-C_{12})$alkyl or $(C_3-C_{12})$alkenyl;
Z is $(C_6-C_{10})$aryl, $(C_3-C_7)$cycloalkyl or a saturated or unsaturated $(C_4-C_7)$ heterocyclic group containing as the heteroatom one or two of the group consisting of oxygen, sulphur, sulphonyl, nitrogen and $NR^4$ wherein $R^4$ is hydrogen or $(C_1-C_4)$ alkyl;
$R^1$ is $(C_1-C_4)$alkyl;
$R^2$ is halo, $(C_1-C_4)$alkyl or $(C_1-C_4)$alkoxy; and
$R^3$ is hydrogen of $(C_1-C_4)$alkyl;
wherein each alkyl, alkoxy, cycloalkyl, aryl or heterocyclic group may optionally be substituted by 1 to 6 halo, $(C_1-C_4)$ alkyl, trifluoromethyl, hydroxy, $(C_1-C_4)$alkoxy, cyano, nitro, $(C_2-C_4)$alkenyl, $(C_3-C_6)$cycloalkoxy, $NR^5R^6$, $CONR^5R^6$, $CO_2R^6$ and $SO_2NR^5R^6$ groups wherein $R^5$ and $R^6$ are each independently hydrogen or $(C_1-C_4)$alkyl;
with the proviso the sum of the atoms defined by W, X and Y is 2 to 18.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl.

The positions on the pyridinyl ring of formula I, as used herein, are defined as follows:

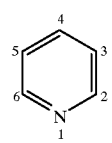

The compounds of formula I include only those structures known to be stable to those skilled in the art.

Preferred compounds of formula I include those wherein b is 1.

Other preferred compounds of formula I include those wherein V is O.

Other preferred compounds of formula I include those wherein W is $(C_4-C_8)$alkyl, X is O and Y is $(C_3-C_7)$alkyl.

Other preferred compounds of formula I include those wherein Z is $(C_6-C_{10})$aryl.

Other preferred compounds of formula I include those wherein $R^1$ is $(C_1-C_4)$alkyl.

Other preferred compounds of formula I include those wherein a is 2 and $R^2$ is chloro in the 3 and 5 positions of the pyridinyl ring.

More preferred compounds of formula I include those wherein b is 1, V is O, W is $(C_4-C_8)$alkyl, X is O, Y is $(C_3-C_7)$alkyl, Z is $(C_6-C_{10})$aryl, $R^1$ is $(C_1-C_2)$alkyl, a is 2 and $R^2$ is chloro in the 3 and 5 positions of the pyridinyl ring.

The present invention also relates to a method for the inhibition of phosphodiesterase (PDE) type IV and the production of TNF comprising administering to a patient an effective amount of a compound according to formula I or a pharmaceutically acceptable salt thereof.

The present invention also relates to a method of treating an inflammatory condition in mammals which comprises administering to said mammal an antiinflammatory amount of a compound of the formula I or a pharmaceutically acceptable salt thereof.

The present invention also relates to a pharmaceutical composition for the (a) treatment of asthma, arthritis, bronchitis, chronic obstructive airways disease, psoriasis, allergic rhinitis, dermatitis and other inflammatory diseases characterized by phosphodiesterase (PDE) Type IV activity, AIDS, sepsis, septic shock and other diseases, such as cachexia, involving the production of TNF, or (b) the inhibition of phosphodiesterase (PDE) type IV and the production of TNF comprising an effective amount of a compound according to formula I or a pharmaceutically acceptable salts thereof together with a pharmaceutically acceptable carrier.

This invention also relates to a method of treating or preventing a condition selected from the group consisting of asthma, arthritis, bronchitis, chronic obstructive airways disease, psoriasis, allergic rhinitis, dermatitis and other inflammatory diseases, AIDS, septic shock and other diseases, such as cachexia, involving the production of TNF comprising administering to a patient an effective amount of a compound according to formula I or a pharmaceutically acceptable salt thereof.

DETAILED DESCRIPTION OF THE INVENTION

The following reaction schemes illustrate, but are not limited to, the preparation of the compounds of the present invention. Unless otherwise indicated a, b, V, W, X, Y, Z, $R^1$ and $R^2$ in the reaction Schemes and the discussion that follow are defined as above.

Preparation A

XIII

H≡≡≡(CH$_2$)$_{\bar{c}}$—AH

↓ 1

-continued

XII

D—(CH$_2$)$_d$—A—(CH$_2$)$_{\bar{c}}$≡≡≡H

↓ 2

XI

[structure with $OR^1$, O—(CH$_2$)$_d$—A—(CH$_2$)$_{\bar{c}}$≡≡≡H, CHO]

Preparation B

XV

Z—(CH$_2$)$_{\bar{c}}$—AH

↓ 1

XIV

Z—(CH$_2$)$_{\bar{c}}$—A—(CH$_2$)$_d$—D

Preparation C

XV

↓ 1

XVII

Z—(CH$_2$)$_{\bar{c}}$—A—(CH$_2$)$_{d-1}$⌇⌇

↓ 2

XVI

Z—(CH$_2$)$_{\bar{c}}$—A—(CH$_2$)$_d$—OH

SCHEME 1

V

[structure with $OR^1$, OH, CHO]

↓ 1

-continued
IV
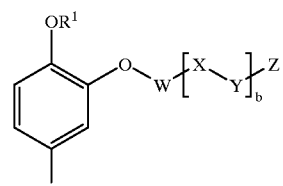
III
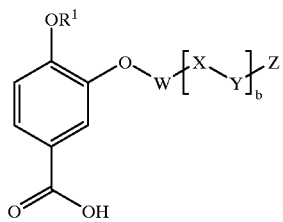
XXI
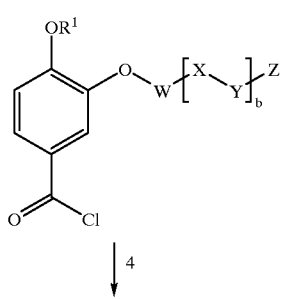
II
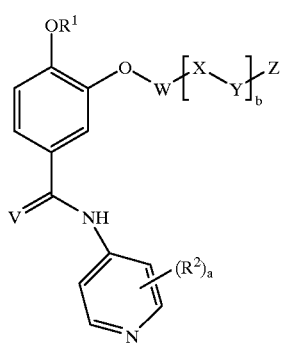
SCHEME 2
X
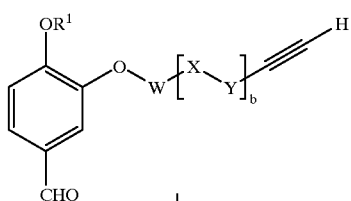
IX
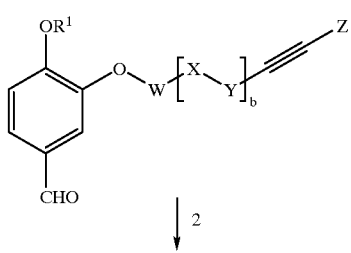
VIII
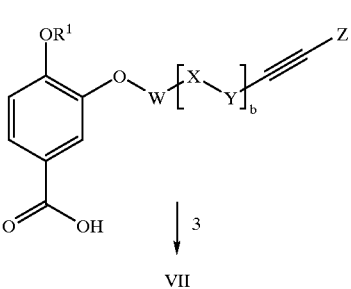
VII
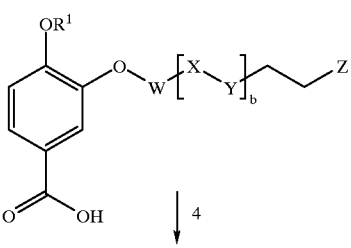

-continued

VI

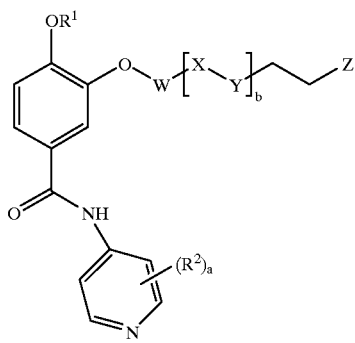

In reaction 1 of Preparation A, the compound of formula XIII, wherein c is 1 to 10 and A is O or $NR^5$ wherein $R^5$ is a protecting group, such as benzyl, is converted to the corresponding compound of formula XII by reacting XIII with a compound of the formula $$D-(CH_2)_d-D \qquad XX$$

wherein D is bromide, iodide, chloride, mesylate or tosylate and d is 2 to 12, in the presence of a base, such as sodium hydride, and a polar aprotic solvent, such as tetrahydrofuran. The reaction mixture is heated to a temperature between about 0° C. to about 100° C., preferably about 62° C., for a time period between about 1 hour to about 24 hours, preferably about 12 hours.

In reaction 2 of Preparation A, the compound of formula XII is converted to the corresponding compound of formula XI by reacting XII with a 3-hydroxy4-alkoxybenzaldehyde compound in the presence of a base, such as potassium carbonate, and a polar aprotic solvent, preferably dimethylformamide. The reaction is heated to a temperature between about 0° C. to about 100° C., preferably about 80° C., for a time period between about 1 hour to about 24 hours, preferably about 3 hours.

In reaction 1 of Preparation B, the compound of formula XV is converted to the corresponding compound of formula XIV according the procedures described above in reaction 1 of Preparation A.

In reaction 1 of Preparation C, the compound of formula XV is converted to the corresponding compound of formula XVII by reacting XV with a compound of the formula

XXII

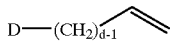

wherein D and d are as defined above, according the procedures described above in reaction 1 of Preparation A.

In reaction 2 of Preparation C, the compound of formula XVII is converted to the corresponding compound of formula XVI by reacting a solution of XVII in a polar solvent, such as methanol, methylene chloride or a mixture thereof, with ozone gas at temperature between about −80° C. to about −50° C., preferably about −78° C., until the solution becomes saturated with ozone. The reaction mixture is then purged with an inert gas, such as nitrogen, and treated with a reducing agent, such as sodium borohydride.

In reaction 1 of Scheme 1, the 3-hydroxy-4-alkoxybenzaldehyde compound of formula V is converted to the corresponding 4-alkoxybenzaldehyde compound of formula IV by alkylating V with a compound of the formula

XIX

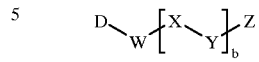

wherein D is as defined above, in the presence of a base, such as potassium carbonate, and a polar aprotic solvent, preferably dimethylformamide. The reaction is heated to a temperature between about 0° C. to about 100° C., preferably about 80° C., for a time period between about 1 hour to about 24 hours, preferably about 3 hours.

An alternative method for the synthesis of the 4-alkoxybenzaldehyde compound of formula IV is to react V with the compound of formula XIX, wherein D is hydroxy, under Mitsunobu conditions (Mitsunobu, O., *Synthesis*, page 1 (1981)).

In reaction 2 of Scheme 1, the 4-alkoxybenzaldehyde compound of formula IV is converted to the corresponding carboxylic acid of formula III by oxidizing IV with sodium chlorite in the presence of an olefin and a polar protic solvent, such as tertbutanol, as described in *Tetrahedron*, 37, 2091 (1981). The carboxylic acid compound of formula III so formed is converted to the corresponding benzoyl chloride compound of formula XXI, in reaction 3 of Scheme 1, by converting III to its corresponding carboxylate and treating it with oxalyl chloride and a catalytic amount of dimethylformamide in a polar aprotic solvent, such as ether, as described in *Tetrahedron Letters*, p. 3379 (1977).

In reaction 4 of Scheme 1, the benzoyl chloride compound of formula XXI is converted to the corresponding benzamide compound of formula II, wherein V is O, by reacting a 4-aminopyridine with a base, preferably sodium hydride, in a polar aprotic solvent, such as tetrahydrofuran, at a temperature between about 0° C. to about 60° C., preferably about 25° C., for a time period between about 30 minutes to about 3 hours, preferably about 30 minutes. A solution of the benzoyl chloride compound of formula II in a polar aprotic solvent, such as tetrahydrofuran, is added to the reaction mixture at a temperature of about 0° C. and the reaction mixture is then stirred at a temperature between about 0° C. to about 40° C., preferably about 25° C., for a time period between about 1 hour to about 24 hours, preferably about 16 hours. The benzamide compound of formula II, wherein V is O, is converted to the thioamide of formula II, wherein V is S, by reacting II with phosphorus pentasulfide in a polar aprotic solvent, such as dioxane, as described in *Synthesis*, page 853 (1982).

In reaction 1 of Scheme 2, the alkyne compound of formula X is converted to the corresponding compound of formula IX by reacting X with an aryl halide or aryl triflate and bis(triphenylphosphine)palladium chloride in an amine solvent, such as diethyl amine, as described in *Bull. Chem. Soc. Jan.*, 63, 640 (1990).

In reaction 2 of Scheme 2, the benzaldehyde compound of formula IX is converted to the corresponding carboxylic acid compound of formula VIII according to the procedure described in reaction 2 of Scheme 1.

In reaction 3 of Scheme 2, the carboxylic acid compound of formula VIII is converted to the corresponding compound of formula VII by hydrogenating VIII in the presence of a metal catalyst, such as platinum, platinum oxide, Raney nickel, rhodium or palladium on carbon, and polar solvent, such as an alcohol, ethyl acetate, tetrahydrofuran, acetic acid or water or a mixture thereof. The reaction temperature is between about 20° C. to about 100° C. and the pressure of hydrogen is between about 1 atmosphere to about 10 atmospheres.

In reaction 4 of Scheme 2, the compound of formula VII is converted to the corresponding benzamide compound of formula VI according to the procedures described above in reactions 3 and 4 of Scheme 1.

The ability of the compounds or the pharmaceutically acceptable salts thereof to inhibit phosphodiesterase IV ($PDE_4$) and, consequently, demonstrate their effectiveness for treating inflammatory diseases is shown by the following in vitro assay.

BIOLOGICAL ASSAY

Human Eosinophil $PDE_4$

Human peripheral blood is collected in ethylenediaminetetraacetic acid, diluted 1:2 in piperazine-N,N'-bis-2-ethanesulfonic acid (PIPES) buffer and then layered over percoll solution. Gradients are formed by centrifugation for 30 minutes at 2000 rpm at 4° C. The remainder of the isolation procedure, which is based on the procedure of Kita et al., J. Immunol., 152, 5457 (1994), is carried out at 4° C. The neutrophil/eosinophil layer is collected from the percoll gradient and the red blood cells are lysed. Remaining cells are washed in PIPES (1% FCS), incubated with anti-CD16 microbeads (MACS) for 1 hour, and passed over a magnetic column to remove the neutrophils. Eosinophils are collected in the eluate and analyzed for viability by trypan blue and purity by diff-quick stain. Eosinophil purity is routinely greater than 99% using this method.

Purified eosinophils are resuspended in 750 $\mu$L of PDE lysis buffer (20 mM triethylamine, 1 mM ethylenediaminetetraacetic acid, 100 $\mu$g/ml bacitracin, 2 mM benzamidine, 50 $\mu$M leupeptin, 50 $\mu$M PMSF, 100 $\mu$g/ml soybean trypsin inhibitor) and quick frozen in liquid nitrogen. Cells are thawed slowly and sonicated. Membranes are vortexed (disruption is confirmed by Trypan blue staining of fragments). Disrupted cells are centrifuged at 45 k rpm for 30 minutes at 4° C. to isolate membranes. Cytosol is decanted, and membrane resuspended to 200 $\mu$g/ml for use as PDE source in the hydrolysis assay yielding a window from 3000 to 5000 counts.

Compounds are dissolved in dimethyl sulfoxide at 10-2M, then diluted 1:25 in water to $4\times10^{-4}$ M. This suspension is serially diluted 1:10 in 4% dimethyl sulfoxide, for a final dimethyl sulfoxide concentration in the assay of 1%.
Phosphodiesterase Inhibition Assay
  To 12×75 mm glass tubes add:
  25 $\mu$l PDE assay buffer (200 mM Tris/40 mM MgC12)
  25 $\mu$l 4 nM/ml cAMP stock
  25 $\mu$l test compound
  25 $\mu$l PDE source (membrane)
  Background control=membrane boiled 10 minutes
  Positive control=25 $\mu$l unboiled membrane
  Incubate 25 minutes in 37° C. water bath.
  Reaction is stopped by boiling samples 5 minutes. Samples are applied to Affigel column (1 ml bed volume) previously equilibrated with 0.25 M acetic acid followed by 0.1 mM N-[2-hydroxyethyl]piperazine-N'-2-ethanesulfonic acid (HEPES)/0.1 mM NaCl wash buffer (pH 8.5). cAMP is washed off column with HEPES/NaCl, 5'-AMP is eluted in 4 ml volumes with 0.25 M acetic acid. 1 ml of eluate is counted in 3 ml scintillation fluid for 1 minute [3H].

Substrate conversion=(cpm positive control×4)/total activity. Conversion rate must be between 3 and 15% for experiment to be valid.

% Inhibition=1-(eluted cpm-background cpm/control cpm-bkgd cpm)×100.

IC50s are generated by linear regression of inhibition titer curve (linear portion); and are expressed in $\mu$M.

TNF

The ability of the compounds or the pharmaceutically acceptable salts thereof to inhibit the production of TNF and, consequently, demonstrate their effectiveness for treating diseases involving the production of TNF is shown by the following in vitro assay:

Peripheral blood (100 mls) from human volunteers is collected in ethylenediaminetetraacetic acid (EDTA). Mononuclear cells are isolated by Ficoll/Hypaque and washed three times in incomplete Hanks' balanced salt solution (HBSS). Cells are resuspended in a final concentration of $1\times10^6$ cells per ml in pre-warmed RPMI (containing 5% FCS, glutamine, pen/step and nystatin). Monocytes are plated as $1\times10^6$ cells in 1.0 ml in 24-well plates. The cells are incubated at 37° C. (5% carbon dioxide) and allowed to adhere to the plates for 2 hours, after which time non-adherent cells are removed by gentle washing. Test compounds (10 $\mu$l) are then added to the cells at 3–4 concentrations each and incubated for 1 hour. Lipopolysaccharide (LPS) (10 $\mu$l) is added to appropriate wells. Plates are incubated overnight (18 hrs) at 37° C. At the end of the incubation period TNF was analyzed by a sandwich ELISA (R&D Quantikine Kit). $IC_{50}$ determinations are made for each compound based on linear regression analysis.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris(hydroxymethyl)-methylammonium salts.

Similarly acid addition salts, such as of mineral acids, organic carboxylic and organic sulfonic acids e.g. hydrochloric acid, methanesulfonic acid, maleic acid, are also possible.

For administration to humans in the curative or prophylactic treatment of inflammatory diseases, oral dosages of the compounds of formula I and the pharmaceutically acceptable salts thereof (hereinafter also referred to as the active compounds of the present invention) are generally in the range of from 0.1–400 mg daily for an average adult patient (70 kg). Thus for a typical adult patient, individual tablets or capsules contain from 0.1 to 50 mg of active compound, in a suitable pharmaceutically acceptable vehicle or carrier. Dosages for intravenous administration are typically within the range of 0.1 to 40 mg per single dose as required. For intranasal or inhaler administration, the dosage is generally formulated as a 0.1 to 1% (w/v) solution. The compound of formula I can also be administered topically in an ointment or cream in concentrations of about 0.5% to about 1%, generally applied 2 or 3 times per day to the affected area. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For administration to humans for the inhibition of TNF, a variety of conventional routes may be used including orally, parenterally and topically. In general, the active compound will be administered orally or parenterally at dosages between about 0.1 and 25 mg/kg body weight of the subject to be treated per day, preferably from about 0.3 to 5 mg/kg. The compound of formula I can also be administered topically in an ointment or cream in concentrations of about 0.5% to about 1%, generally applied 2 or 3 times per day to the affected area. However, some variation in dosage will necessarily occur depending on the condition of the subject being treated. The person responsible for administration will, in any event, determine the appropriate dose for the individual subject.

For human use, the active compounds of the present invention can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules or ovales either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substances; for example, enough salts or glucose to make the solution isotonic.

The present invention is illustrated by the following examples, but it is not limited to the details thereof.

Preparation 1

4-Methoxy-3-(11-phenylundecyloxy)benzoyl chloride

To a magnetically stirred solution of 4-methoxy-3-(11-phenylundecyloxy)benzaldehyde (2.4 grams) and 2-methyl-2-butene (27 ml) in tert-butanol (50 ml) is added a solution of sodium chlorite (4.5 grams) and sodium phosphate, monobasic (4.5 grams) in water (50 ml) over 10 minutes. After stirring for 1 hour at room temperature the volatile organics are removed under reduced pressure and the resulting aqueous mixture is acidified to a pH of 1 with 1N hydrochloric acid and extracted with ethyl acetate. The combined organics are washed with water and brine, dried over sodium sulfate and concentrated under reduced pressure to give 2.3 grams of a yellow oil.

To a solution of the above oil in methanol (20 ml) at room temperature is added sodium methoxide (0.3 grams). After 30 minutes the methanol is removed under reduced pressure, anhydrous toluene is added and then removed under reduced pressure, anhydrous toluene is added and then removed under reduced pressure. The resulting white solid is suspended in anhydrous ether (25 ml) at 0° C. under a nitrogen atmosphere and oxalyl chloride (20 ml) and dimethylformamide (1 drop) are added. After stirring for 1 hour at 0° C. the reaction mixture is filtered and concentrated to a yellow oil (2.3 grams). This oil is used immediately.

Preparation 2

4-Methoxy-3-(11-phenylundecyloxy)benzaldehyde

To a solution of 3-hydroxy-4-methoxybenzaldehyde (2.5 grams), 11-phenylundecylalcohol (4.6 grams) and triphenylphosphine (4.9 grams) in tetrahydrofuran at 0° C. is slowly added diethyl azodicarboxylate (2.9 ml). After stirring for 2 hours at room temperature the mixture is concentrated under reduced pressure and purified by column chromatography on a silica gel column using a 9:1 mixture of hexane and ethyl acetate as eluent to give 2.4 grams of a yellow oil. $^1$H NMR (CDCl$_3$) δ $^1$H NMR (CDCl$_3$) δ 0.82–1.89 (m, 18H), 2.35–2.70 (m, 2H), 3.95 (s, 3H), 4.00–4.08 (m, 2H), 6.95–7.45 (m, 8H), 9.84 (s, 1H).

Preparation 3

4-Methoxy-3-[6-(4-phenylbut-1-yloxy)hex-1-yloxy] benzaldehyde

To a stirred solution of 3-hydroxy-4-methoxybenzaldehyde (4.8 grams) in dimethylformamide (100 ml) at room temperature is added potassium carbonate (4.9 grams) and 1-bromo-6-(4-phenylbut-1-yloxy)hexane (10.0 grams). After stirring at 80° C. over 4 hours the reaction mixture is poured into water and extracted with ethyl acetate. The combined organics are washed with 1N sodium hydroxide and brine, dried over sodium sulfate, filtered and concentrated under reduced pressure. The resulting amber oil is filtered through a 5×10 cm pad of silica gel, eluting with a 1:3 mixture of ethyl acetate and hexane, to give 12.0 grams of a colorless oil. MS (m/z) 384.

Preparation 4

4-Methoxy-3-[6-(6-phenylhex-1-yloxy)hex-1-yloxy]benzaldehyde

Reaction of 1-bromo-6-(6-phenylhex-1-yloxy)hexane and 3-hydroxy-4-methoxy benzaldehyde analogous to the procedure of preparation 3, affords the title compound as a pale yellow oil. MS (m/z) 413.

EXAMPLE 1

N-(3,5-dichloropyrid-4-yl)-4-methoxy-3-(11-phenylundecyloxy)benzamide)

To a magnetically stirred suspension of 60% sodium hydride (60% in mineral oil) (0.53 grams) in anhydrous tetrahydrofuran (20 ml) at 0° C. is added a solution of 4-amino-2,5-dichloropyridine (0.90 grams) in anhydrous tetrahydrofuran (20 ml). After stirring for 30 minutes at room temperature the reaction mixture is cooled to 0° C. and treated with a solution of 4-methoxy-3-(11-phenylundecyloxy)benzoyl chloride (2.30 grams) in tetrahydrofuran (20 ml). After stirring at room temperature for 16 hours the reaction mixture is poured into 50 ml of 1N hydrochloric acid and extracted with ethyl acetate. The combined organics are washed with 1N hydrochloric acid, water and brine and then dried over sodium sulfate and concentrated under reduced pressure. The resulting yellow solid is purified by column chromatography on a silica gel column using a ratio of 9:1 mixture of methylene chloride and ethyl acetate as eluent to give 1.9 grams of an off-white solid. MP 114–5° C.; MS m/z 543, 545; Anal. calcd for $C_{30}H_{36}Cl_2N_2O_3$: C, 66.29; H, 6.68; N, 5.15. Found: C, 6646; H, 6.61; N, 5.08

EXAMPLES 2–3

Reaction of the appropriate benzoyl chloride with 4amino-2,5-dichloropyridine, analogous to the procedure of Example 1, affords the following compounds of formula II, wherein V is O, $R^1$ is methyl, a is 2 and $R^2$ is chloro in the 3 and 5 positions on the pyridinyl ring.

| Ex# | W-[X-Y]$_b$-Z | MP° C. | MW | HRMS or Analysis (calcd.) %C, %H, %N | HRMS or Analysis (found %CV, %H, %N |
|---|---|---|---|---|---|
| 2 | (CH$_2$)$_6$O(CH$_2$)$_4$-phenyl | 111–2 | 545.5 | [M + H]545.1974 | HRMS [M + H]545.1956 |
| 3 | (CH$_2$)$_6$O(CH$_2$)$_6$-phenyl | 115–6 | 573.6 | 64.92, 6.68, 4.88 | 65.13, 6.60, 4.99 |

We claim:

1. A compound of the formula

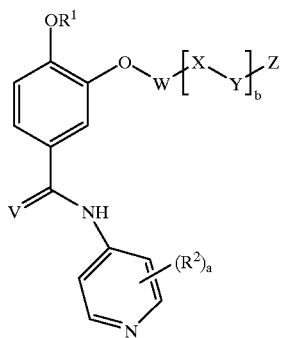

I or a pharmaceutically acceptable salt thereof; wherein
a is 0, 1, 2, 3 or 4;
b is 0, 1, 2, 3 or 4;
V is O or S;
W is (C$_2$–C$_{12}$)alkyl or (C$_3$–C$_{12}$)alkenyl;
X is O or NR$^3$;
Y is (C$_1$–C$_{12}$)alkyl or (C$_3$–C$_{12}$)alkenyl;
Z is (C$_6$–C$_{10}$)aryl, (C$_3$–C$_7$)cycloalkyl or a saturated or unsaturated (C$_4$–C$_7$) heterocyclic group containing as the heteroatom one or two of the group consisting of oxygen, sulphur, sulphonyl, nitrogen and NR$^4$ wherein R$^4$ is hydrogen or (C$_1$–C$_4$) alkyl;
R$^1$ is (C$_1$–C$_4$)alkyl;
R$^2$ is halo, (C$_1$–C$_4$)alkyl or (C$_1$–C$_4$)alkoxy; and
R$^3$ is hydrogen or (C$_1$–C$_4$)alkyl;
wherein each alkyl, alkoxy, cycloalkyl, aryl or heterocyclic group may optionally be substituted by 1 to 6 halo, (C$_1$–C$_4$) alkyl, trifluoromethyl, hydroxy, (C$_1$–C$_4$)alkoxy, cyano, nitro, (C$_2$–C$_4$)alkenyl, (C$_3$–C$_6$)cycloalkoxy, NR$^5$R$^6$, CONR$^5$R$^6$, CO$_2$R$^6$ and SO$_2$NR$^5$R$^6$ groups wherein R$^5$ and R$^6$ are each independently hydrogen or (C$_1$–C$_4$)alkyl;
with the proviso the sum of the atoms defined by W, X and Y is 2 to 18.

2. A compound according to claim 1, wherein b is 1.

3. A compound according to claim 1, wherein V is O.

4. A compound according to claim 1, wherein W is (C$_4$–C$_8$)alkyl, X is O and Y is (C$_3$–C$_7$)alkyl.

5. A compound according to claim 1, wherein Z is (C$_6$–C$_{10}$)aryl.

6. A compound according to claim 1, wherein R$^1$ is (C$_1$–C$_2$)alkyl.

7. A compound according to claim 1, wherein a is 2 and R$^2$ is chloro in the 3 and 5 positions of the pyridinyl ring.

8. A compound according to claim 1, wherein b is 1, V is O, W is (C$_4$–C$_8$)alkyl, X is O, Y is (C$_3$–C$_7$)alkyl, Z is (C$_6$–C$_{10}$)aryl, R$^1$ is (C$_1$–C$_2$)alkyl, a is 2 and R$^2$ is chloro in the 3 and 5 positions of the pyridinyl ring.

9. A method for the inhibition of phosphodiesterase (PDE) type IV and the production of tumor necrosis factor (TNF) comprising administering to a subject an effective amount of a compound according to claim 1 or a pharmaceutically acceptable salt thereof.

10. A method of treating an inflammatory condition in mammals which comprises administering to said mammal an antiinflammatory amount of a compound according to claim 1 or a pharmaceutically acceptable salt thereof.

11. A method of treating a condition selected from the group consisting of asthma, arthritis, bronchitis, chronic obstructive airways disease, psoriasis, allergic rhinitis, dermatitis and other inflammatory diseases, AIDS, septic shock and cachexia, involving the production of TNF comprising administering to a patient an effective amount of a compound according to claim 1 or a pharmaceutically acceptable salt thereof.

12. A pharmaceutical composition for the (a) treatment of asthma, arthritis, bronchitis, chronic obstructive airways disease, psoriasis, allergic rhinitis, dermatitis and other inflammatory diseases which have phosphodiesterase (PDE) type IV activity, IDS, sepsis, septic shock and cachexia, involving the production of TNF, or (b) the inhibition of phosphodiesterase (PDE) type IV and the production of tumor necrosis factor (TNF) comprising a pharmaceutically effective amount of a compound according to claim 1 and a pharmaceutically acceptable carrier.

* * * * *